United States Patent
Schmidt et al.

(10) Patent No.: US 7,066,883 B2
(45) Date of Patent: Jun. 27, 2006

(54) METHOD AND SYSTEM FOR MONITORING THE COURSE OF THERAPY OF A PATIENT BEING THERAPEUTICALLY TREATED

(75) Inventors: Volker Schmidt, Erlangen (DE); Siegfried Schneider, Erlangen (DE); Sven Tiffe, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 735 days.

(21) Appl. No.: 10/139,834

(22) Filed: May 7, 2002

(65) Prior Publication Data

US 2002/0169366 A1 Nov. 14, 2002

(30) Foreign Application Priority Data

May 10, 2001 (DE) ............................. 101 22 778

(51) Int. Cl.
*A61B 5/00* (2006.01)
(52) U.S. Cl. .................. 600/300; 128/920; 604/65
(58) Field of Classification Search ........ 600/300–301; 128/903–906, 920–925; 340/573.1–576, 340/539.1; 705/2–4; 604/890.1, 131, 65–67
See application file for complete search history.

(56) References Cited

U.S. PATENT DOCUMENTS

| | | | | |
|---|---|---|---|---|
| 5,724,025 | A | * | 3/1998 | Tavori .................... 600/300 |
| 5,749,907 | A | | 5/1998 | Mann |
| 6,024,699 | A | * | 2/2000 | Surwit et al. ............ 600/300 |

* cited by examiner

*Primary Examiner*—Max F. Kindenburg
*Assistant Examiner*—Michael Astorino
(74) *Attorney, Agent, or Firm*—Schiff Hardin LLP

(57) ABSTRACT

In a method and system for monitoring the course of therapy administered to a patient, at least one information value that requires a therapeutic and/or diagnostic measure and that is a direct or indirect measure of the course of the therapy is registered continuously or in time intervals, and at least one comparison value, to be compared to the information value or to a calculated value determined based on the information value, is allocated to the information value. An alarm signal is emitted given an impermissible deviation of the information value or of the calculated value from the comparison value and is detected in the course of the comparison. The comparison value is varied dependent on the course of the therapy and is adapted to the course of the therapy, the adaptation of ensuing automatically or by means of an authorized person or entity.

20 Claims, 2 Drawing Sheets

METHOD AND SYSTEM FOR MONITORING THE COURSE OF THERAPY OF A PATIENT BEING THERAPEUTICALLY TREATED

BACKGROUND OF THE INVENTION

1. Field of the Invention

The present invention is directed to a method for monitoring the course of therapy of a patient to be therapeutically treated, of the type wherein at least one information value that requires a therapeutic and/or diagnostic measure and that is a direct or indirect measure of the course of the therapy is registered continuously or in time intervals, and to which at least one comparison value to be compared thereto or to a calculated value determined based on the information value is allocated, wherein an alarm signal is emitted given a inadmissible deviation from the comparison value by the information value or the calculated value and is detected in the course of the comparison, and whereby the comparison value is varied dependent on the course of the therapy and is adapted to the course of the therapy.

2. Description of the Prior Art

When one or various health-related values or parameters of a patient lie outside a defined normal range, then an attempt is made to set this value or this parameter of the patient to a target range that usually corresponds to this normal range by means of a suitable, targeted therapy. An example is a patient with high blood pressure. The health-related value in this case would be blood pressure, measurable in a simple way, that must be lowered so that it lies in a desired, target range. This phase, which is usually called the setting phase, can be time-limited; the monitored value or values should have reached the target range no later then the end of the setting phase. When the patient has been set, then the values are monitored in the following maintenance phase.

When the values leave a defined value range during the setting or maintenance phase, which can be acquired by comparing the registered value or parameters to comparison values defining the value range, then a change in the treatment method as well as further measures such as, for example, diagnostics, etc., can become necessary. When the registered value changes toward the positive, i.e. when an improvement occurs (therapeutically positive effect), then no disadvantage arises for the patient. When, however, the value changes in a negative way, then a responsible person or entity, for example a physician, must be made aware of this. An alarm signal must thus be emitted that indicates a negative condition. Rigid alarm limits are employed in known systems. This, however, frequently leads to false alarms or to an absence lack of alarms when an unstable system adjusts itself to a stable value. For example, such a method or system is utilized in intensive medicine for stationary treatment, whereby an automatic monitoring of critical vital parameters is undertaken.

U.S. Pat. No. 5,749,907 discloses a method with the features initially cited. Deviations of the registered information value from a comparison value can be acquired with this method, and the physician located on site can be notified during a visit, and the physician has the possibility of also taking information values registered temporally earlier into the comparison. Further, the physician has the possibility of modifying the comparison value when the physician interacts with the patient.

SUMMARY OF THE INVENTION

An object of the present invention is to provide an improved method with more dependable and more reliable notification.

This object is achieved in a method and system of the type initially described, wherein the adaptation of the comparison value ensues automatically or by means of an authorized person or entity (i.e., an agent), at predetermined time intervals or at variable time intervals, dependent on the registered information value or on the determined calculated value, and wherein, given an adaptation carried out by a person or entity, the person or entity is made automatically aware of the need for adaptation.

At least one information value is registered in the inventive method. This can be a direct measure of the course of the therapy. For example, blood pressure can be measured as the information value, or the information value can be a value describing blood coagulation, insulin level or the like. The information value, however, can be an indirect measure of the course of the therapy. For example, the exhalation rate or the exhaled volume can be used in the case of an asthmatic, and conclusions about the condition of the bronchia can be made on the basis thereof.

This information value, that can be continuously registered, or registered at a freely selectable uniform or non-uniform time interval, can have a comparison value directly allocated thereto that sets a limit with which the information value must lie in a specific relationship. Alternatively, there is the possibility of determining a calculated value on the basis of this information value, and further-processing this calculated value, for example linking it with further information values that were registered or to other information values relevant to the therapy, or to link a number of information values that were registered at different times with one another. This calculated value is also compared to the comparison value in order to determine a permissible or impermissible deviation or an inadmissible or admissible relationship of the calculated value to the comparison value. When the information value or the calculated value lies in a permissible relationship or exhibits a permissible deviation with respect to the comparison value, then it is not necessary to emit an alarm since the therapy course is positive, i.e. beneficial and as desired. When, however, the comparison has an inadmissible deviation from the comparison value or an inadmissible deviation that will shortly occur on the basis of a trend analysis produced with reference to the calculated value, then an alarm must be emitted to a responsible person or entity.

In an embodiment of the inventive method the comparison value is not rigid but is variably selected dependent on the course of therapy and can be adapted to the course of the therapy. When, thus, the patient is in, for example, the setting phase wherein high blood pressure is to be lowered to a normal blood pressure, then a high comparison value is allocated to the information value or calculated value at the beginning of the treatment, i.e. when the information value or the calculated value are correspondingly high. As the course of the treatment proceeds and given a positively proceeding therapy, the information value or calculated value is lowered. This is accomplished with the allocated comparison value that is likewise correspondingly lowered. If the blood pressure rises again in an unpredicted way and lies above the adapted comparison value, an alarm signal is emitted since this condition is recognized as an alarm condition on the basis of the adaptation of the comparison value. If a rigid comparison value limit were defined that would necessarily have to be defined in view of the high initial blood pressure value, then no alarm signal would be emitted in the described case since the rigid comparison or alarm limit would not have been exceeded given an increase in the blood pressure that was already therapeutically lowered.

According to the inventive method, the comparison value can be arbitrarily varied and adapted in view of the course of the therapy, i.e., for example, it can be continuously lowered in steps or stages given a continuously occurring lowering of blood pressure. In this way, it is possible to correlate the monitoring of the value and the output of the alarm with one another in such a way that the actual condition is also taken into consideration.

This inventive method, of course, can be arbitrarily applied in addition to the described application of the method in the content of blood pressure measurement. For example, the monitoring of the blood coagulation is a further example. The patient, as can be the case as well when measuring blood pressure, personally determines the information value at home, i.e. the blood coagulation value here, that is then processed as described. The same is true for a diabetic patient who, for example, acquires his or her blood sugar value and his or her weight at time intervals, so that two information values enter into the comparison in this example Further combinations are also possible, for example in the case of a diabetic with high blood pressure. The diabetic-related information values are acquired as well as a blood pressure value, since the relevant parameters can definitely disadvantageously influence one another from a therapeutic point of view. Consequently, both must be considered in the evaluation as to whether an adaptation of the comparison value is expedient and required. In such a case, for example, a beta blocker administered to counter high blood pressure has a disadvantageous effect on the insulin level.

Inventively, the adaptation of the (at least one) comparison value can automatically ensue by means of a suitable adaptation device of a control system. This adaptation device, for example, can be a central computer device that receives all relevant information values and wherein the relevant comparison values are deposited, and that controls all comparison operations and other calculating operations as well as the output of alarms and other information. Alternatively, an authorized person or an authorized entity, for example a physician or the responsible persons within a physician's practice or a clinic, undertake this adaptation when they have the comparison results are made available. It is expedient for the central system control to instruct the person or the entity about the requirement of adaptation given a manual adaptation to be carried out by a person or entity.

The adaptation of the comparison value or values can ensue at predetermined time intervals or at variable time intervals. A temporally prescribed adaptation can, for example, be implemented such that, after determination of the requirement of adaptation, this ensues at a specific point in time; a time-variable adaptation can ensue at any arbitrary point in time, for example immediately after determination of the requirement for an adaptation. Which adaptation mode is selected can be dependent on the registered information value or on the determined calculated value.

For example, a monitoring system as disclosed by European Application 00 124 669 can be employed for the implementation of the inventive method, the teachings of which are incorporated herein by reference.

Since a monitored value or parameter should usually lie within specific limits, it is advantageous when upper and lower comparison values are allocated to the information value or to the calculated value, with the information value or the calculated value being compared to both in order to check whether it is in the defined interval. An impermissible deviation exists when the information value or the calculated value lies above the upper or below the lower comparison value.

In addition to the comparison of a single registered information value or a single determined calculated value, it can be advantageous in the inventive method to predict that am impermissible deviation that will occur in the near future and to implement a comparison of a therapy trend determined by analysis of information values registered earlier in time or calculated values that have been determined, to the comparison value. This is a trend analysis that indicates a specific, future course of the therapy, and this indicated course is taken into consideration in the comparison. When, for example, it turns out in the context of blood pressure monitoring that a rising trend is present within the last four or five blood pressure values that were measured, then an alarm can be emitted when, for example, the most recently registered value lies close to, for example, the upper comparison value limit but still lies within the allowable range. This is because it must be expected that the next value that is registered will either continue the trend or already will lie above the comparison value. The course of the therapy that can be predicted is thus utilized in order to emit an alarm in advance.

As described, it is conceivable to take only one information value or a calculated value based thereon, into consideration in the comparison and the adaptation of the comparison value. However, the adaptation can be undertaken dependent on a number of different, registered information values or determined calculated value to which at least one separate comparison value is then respectively allocated. For example, it may be that a negative effect with respect to another symptom that is likewise to be therapeutically treated occurs due to the administration of a medication that serves the purpose of treating a specific symptom. For example, given administration of beta blocker serving the purpose of lowering blood pressure, a poor insulin value can occur, i.e. the two values are correlated with one another in this respect. This knowledge, namely that a beta blocker was administered, is relevant for emitting the alarm signal or for the adaptation of, for example the insulin comparison value as well, since it can be determined is that the deterioration of the insulin value is to be attributed to the administration of the beta blocker and not to a general deterioration of the health of the patient.

The adaptation itself can ensue dependent on the comparison of the information value or of the calculated value to the (at least one) comparison value such that the adaptation is undertaken given an admissible deviation from the comparison value. When, for example, it is intended that the registered information value or the calculated value based thereon become lower during the setting phase, and if this lies within a specific value interval around the lower limit of the comparison interval defined by two comparison values, then the information value deviates permissibly from both comparison values (it is lower than the upper and higher then the lower comparison value), and it approaches the lower interval limit, this indicates that an adaptation by lowering the defined comparison value interval toward lower interval values is required. Alternatively, the adaptation can ensue dependent on a therapy trend determined from the registration of temporally earlier information values or calculated values that were determined earlier. In any case, it must be assured that the adaptation is justified with respect to the condition of the patient.

Further, a tolerance value range can be allocated to each comparison value. This assures that a slight upward or downward transgression of a comparison value, which strictly would lead to the emission of an alarm, does not lead to the emission of the alarm but is classified as a brief-duration, impermissible deviation that can be accepted. Of course, it must be assured that a persistent deviation without emitting an alarm information is precluded. For example, a defined number of impermissible deviations can be identified without having an alarm signal being output. Given another impermissible deviation and an upward transgression of the defined number, the alarm is then immediately emitted.

In a further embodiment the responsible person or entity is provided with a warning if a desired success of the therapy, that can be indicated by the registration of the information value or the determination of the calculated value does not occur within a predetermined time interval. This is intended to avoid the monitoring system continuing to operate with the patient continuously subjected to therapy in the same way without the desired success of the therapy occurring or the goal of the therapy being achieved or even being approached. This embodiment of the invention assures that a warning is forwarded to the attending physician or the like if a specific target value does not occur within a predetermined time interval. This also can ensue, for example, on the basis of the comparison values. When the information value or the reference value has a comparison value interval allocated to it that is defined by an upper and a lower comparison value, then given a targeted lowering of the respective parameter or system to be therapeutically treated, for example blood pressure, a time interval value can be allocated to the lower comparison value, and the alarm is emitted when the information value or the calculated value within the time interval defined by this time interval value does not exhibit any permissible deviation from or approach to the comparison value. If the blood pressure value is intended to continuously decrease, an adequate approach to this final comparison value or a downward transgression thereof is defined as permissible deviation. As a result, it is assured that the monitoring system does not rigidly monitor a condition is not changing or changes only insignificantly; rather, it monitors the success of the therapy in a quasi self-monitoring fashion and supports the attainment of the objective of the therapy.

It is particularly expedient for achieving the inventive objective when the person or the entity, in addition to being provided with the information about the non-attainment of the goal of the therapy, is provided with further therapeutically or diagnostically relevant information that are read from a knowledge data bank that is contained in the system. This information can, for example, contain alternative therapy or treatment methods other than those being applied at the moment and obviously not leading to success, or can include other therapeutic or diagnostically relevant information. Of course, such information also can be generally made available during the on-going monitoring. To this end, the use of a knowledge data bank contained in the system is expedient, for example in the form of the "Arden Syntax for Medical Logic System". Such knowledge data banks are known; their incorporation into the present method is advantageous for further improving the monitoring method and system in view of achieving the objective of the treatment optimally and as expeditiously as possible.

As already described, the system suitable for the implementation of the inventive method includes a calculating or system central or system control that receives the relevant information values, and which may also determine the calculated values or implement trend analyses, and also implements all other comparison and calculating operations and the output of relevant information, whether in the form of an alarm or information from its knowledge data bank or the like. The adaptation of the at least one comparison value is undertaken by this calculating or system central. In this context, it is generally expedient when an expert system is employed, particularly for the implementation of the described steps, functioning in a supportive fashion. This expert system obtains its data from a data bank or from a network and, dependent on the patient to be therapeutically treated as well as on the symptom to be therapeutically treated and on the course of the therapy, generates information that is emitted as needed.

As already described, the method can be implemented with an arbitrary monitoring system that allows the registration of the relevant information value or values as well as the corresponding interpretation thereof. This can be a central or a decentralized system; different system versions are also conceivable. For example, the acquisition of the information value can ensue at the home of the patient; the transmission of the information values can ensue via a computer at the location of the patient, to a calculating or system central that then undertakes the corresponding evaluations and steps. The evaluation also can be undertaken at the location of the patient, with the emissions of an alarm signal, when necessary, ensuing via a communication network to the recipient, controlled, for example, via the computer at the patient. The employment of a cell phone for transmission of the information values, etc., is also conceivable. In this context, the techniques described in European Patent Application 00 124 669 that was previously cited can be used.

In addition to the inventive method, the invention is also directed to a system for monitoring the course of the therapy of a patient to be therapeutically treated that is suitable for the implementation of the described method.

DESCRIPTION OF THE PREFERRED EMBODIMENTS

Figure 1:
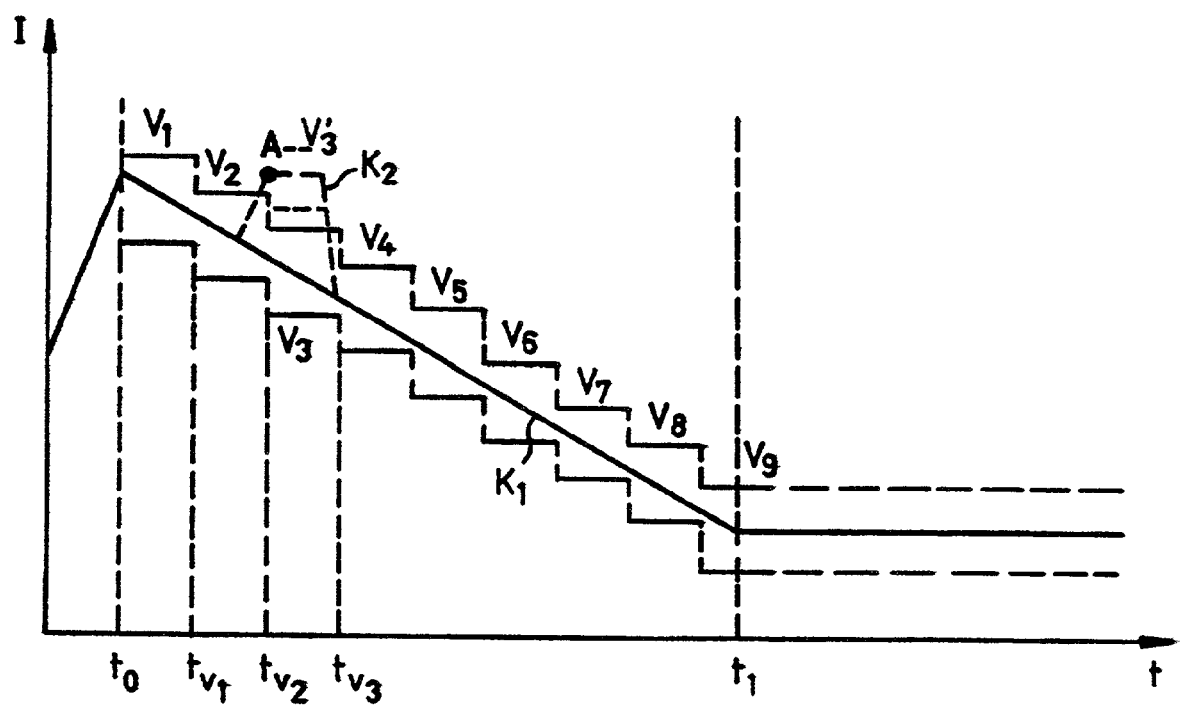
FIG. 1 is a diagram for showing the basic principle of the inventive method.

FIG. 1 is a diagrammatic flowchart of the inventive method. Time is shown along the abscissa and the information value I is shown along the ordinate. As can be seen, the information value I rises rapidly at the beginning of the curve, i.e. a pathological symptom occurs. Blood pressure of the patient clearly increases. The blood pressure, for example, is monitored by the patient at home using a suitable blood pressure measuring device, and the measured values are transmitted to an external, central computer or to a system control unit, for example via an input computer at the location of the patient. In this central computer or this system control unit, the information value in the illustrated example is directly considered without being converted into a calculated value. At the control unit, a comparison value pair is allocated to the information value I at point in time $t_0$ that defines the beginning of the setting phase, i.e. the beginning of the therapy for lowering blood pressure, with upper and a lower comparison values defining a comparison value interval with reference to the information value. At either continuous or discontinuous intervals, for example everyday, the patient then measures the blood pressure and transmits the information values. These are respectively compared to the comparison values of the comparison value pair $V_1$ and a check is made to determine whether the information value lies within this comparison value interval and whether, in particular, it does not exceed the upper comparison value, i.e. has continued to rise. As can be seen, the information value in the illustrated exemplary embodiment continuously decreases during the setting phase between $t_0$ and $t_1$. With continuing decrease, the information value approaches the lower comparison value of the comparison value pair $V_1$. Beginning with a specific approach—or when this lower value is downwardly transgressed—, the central system control device allocates a new comparison value pair $V_2$ to the information value I, whereby the upper and the lower comparison value are lowered by a specific amount. In the ideal case, shown with the solid-line curve $K_1$, blood pressure decreases continuously given an optimum course of the therapy until it reaches a normal value at time $t_1$, which should be maintained in the setting phase that follows the point in time $t_1$. With the continuous decrease, the continuous comparison of the registered actual information value to the comparison value pair $V_1$ always checks whether the information value lies within the allowable range. When this is confirmed, a continuous check is likewise carried out to determine whether an adaptation of the comparison value pair is required and, if so, to undertake the necessary change. The respective comparison value pair can be adapted to the course of the therapy such that it is correlated by a rating in terms of quantity to the actual information value.

Curve $K_1$ shows the optimum course of the therapy, i.e. a continuous improvement occurs. If the situation occurs during the course of the therapy that the information value—for whatever reason—does not change in the direction of the desired objective of the therapy, but impermissibly rises, and given deterioration of the patient's condition, as shown by the broken-line curve $K_2$, then the registered information value migrates out of the defined comparison value interval, i.e. an impermissible deviation of the information value from the upper comparison value occurs. This situation is shown in FIG. 1 with the point reference A. Given an impermissible deviation acquired as a result of the comparison of the information value to the comparison values, an alarm is immediately emitted to a responsible person, informing that person that a noticeable, rapid and inadmissible change of the condition is present in the monitored patient. The attending physician can immediately have recourse to counter measures. At the same time, a renewed adaptation of the comparison value interval ensues in the system, this being significantly increased in the illustrated example in view of the rapidly rising information value and being shown in FIG. 1 with the comparison interval $V_3'$. As can be seen, the therapy measure immediately introduced by the attending physician, for example administration of stronger medications or other medications or some other modification of the treatment method, exhibits an effect, since the curve $K_2$ in turn clearly drops. The information value I again approaches normal values, as the optimum course of the therapy would have allowed one to expect. Subsequently, no further difficulties occur given the illustrated strategy and the information value, i.e. the blood pressure value, drops continuously until the objective of the therapy is achieved at time $t_1$. The comparison value pair $V_9$ is allocated to this point in time, this comparison value pair $V_9$ also being retained in the maintenance phase. Therein, a re-checking expediently occurs up to a specific point in time in order to assure that the blood pressure value also remains in the allowable normal range.

Even though FIG. 1 only describes taking an information value into consideration within the framework of the inventive method, it is conceivable to consider two or more different information values during the course of the comparison and the adaptation examinations and the evaluations. FIG. 1 is only of an exemplary nature.

Figure 2:
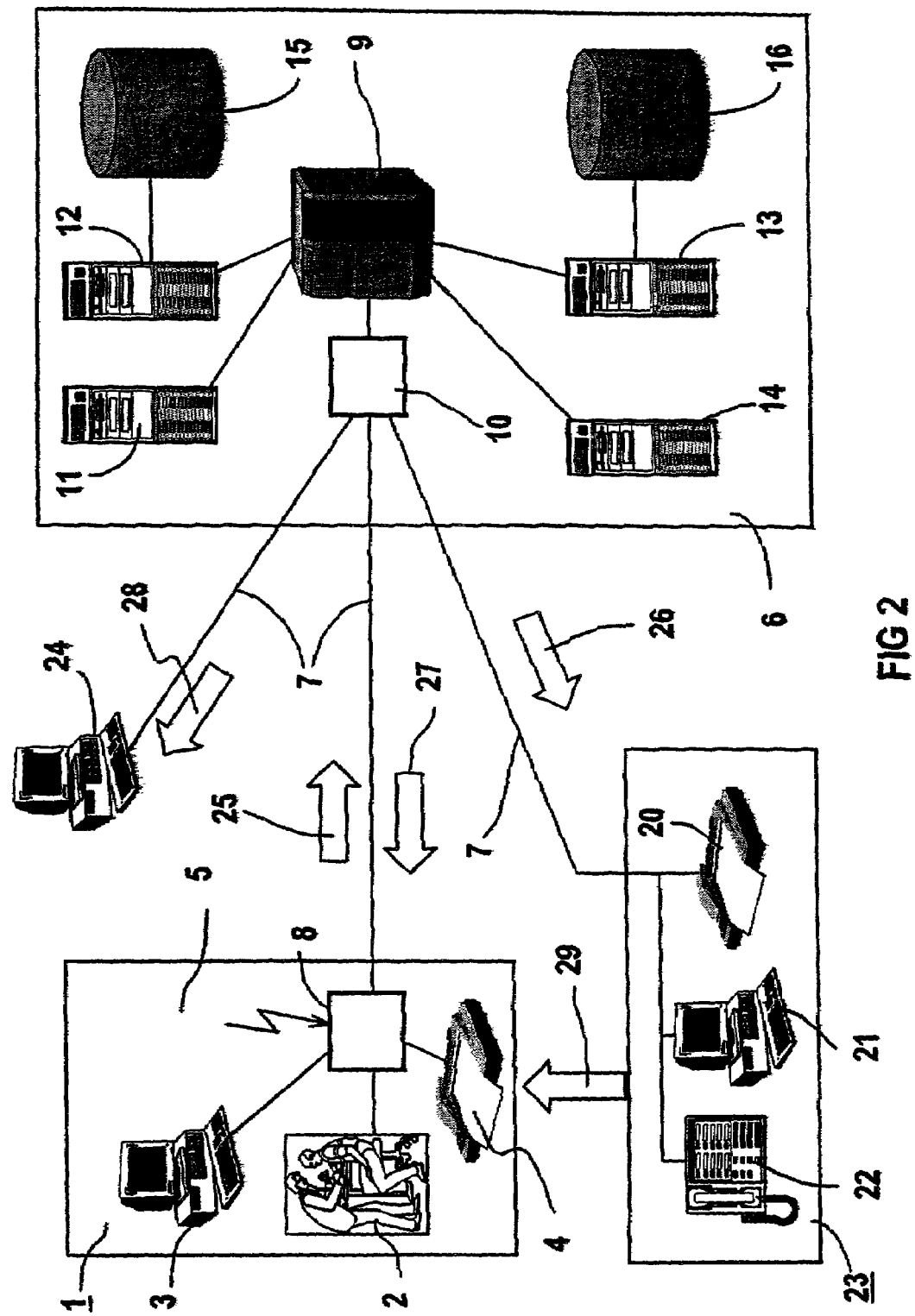
FIG. 2 is a schematic illustration of a system suitable for the implementation of the method.

FIG. 2 shows an inventive system for continuous monitoring of medical parameters of a patient at home 1 and, thus, for the implementation of the inventive method, wherein the measured value acquisition 2 ensues either automatically or manually by the patient or physician or by a care giver. These measured or information values can be directly forwarded to a system central 6 by personal computer 3, with a fax machine 4 or by telephone or cell phone 5. This, for example, can ensue via an ISDN network 7 to which the corresponding terminal devices are connected via an ISDN interface 8.

A gateway 9 is provided in the system central 6, the gateway 9 being connected to the ISDN network 7 via an ISDN interface 10. An Internet server 11 for access to the Internet, an evaluation device 12 for the measured or information values, a patient data server 13 for the administration of the patient data and a communication server 14 as routing device for collaboration of all components and forwarding messages can be connected to the gateway 9. A data memory 15 for the measured values is connected to the evaluation device 12 and a data bank 16 as memory device is connected to the patient data server 13.

The evaluation device 12 includes a comparator for comparing the measured or information values to reference values stored in the data memory 15 and comprises an alarm device for generating an alarm signal given upward transgression of the measured values above stored comparison limits. As required, it undertakes the generation of potential calculated values, potential trend analyses as well as, possibly, the adaptation of the comparison values.

Reception devices such as, for example, a fax machine 20, personal computer 21 or a telephone 22 or cell phone are connected to the system central 6, these belonging to an on-call physician and, for example, can be arranged in a shared practice 23 of physicians.

A personal computer 24 of a practice of an attending physician is also connected via the ISDN network 7 to the gateway 9 of the system central 6.

The medical data are read in in the system central 6 via standardized telecommunication interfaces and are stored long-term in the data memory 15; the evaluation device 12 evaluates the medical data and the point in time of the data transmission in order to be able to send information messages. The data transmission ensues, for example, via the Internet or the telephone network. Assigning a patient identification number ensues via a security architecture.

All information that are required for the realization of the specific embodiments of the alarm generator and for realizing a forward of messages given the absence of the recipient can be merged in the system central 6.

The terminal device 2 through 5 for the patient serve the purpose of acquiring the medical data at the patient and transmitting the data to the system central 6. Arbitrary existing devices of measurement technology can be employed, for example ECG, blood pressure, blood sugar measuring devices, test strips, peak flow meters and/or vital capacity measuring devices. The data forwarding 25 of the measured or information values to the server in the system central 6 can ensue by means of the measuring instrument itself or can be realized by input possibilities described below.

A personal digital assistant (PDA) or a lap top is provided for the care givers, all patient data of patients that are visited by this care-giver service being input thereinto. The synchronization of the data can ensue immediately, for example via a cell phone Internet connection, or can ensue at a later point in time when the nurse arrives back in the office or practice.

The system central 6 serves the purpose of receiving medical data via one of the telecommunication interfaces and storing it in the data memory 15. Additionally, it should undertake a further-processing of the medical data with the assistance of the evaluation device 12 for the measured or information values with the alarm device and the data memory 15. An output of the data acquired in the data memory 15 to one of the terminal devices for physicians ensues via a telecommunications interface.

The alarm device in the evaluation device 12 triggers an alarm given the presence of one of the event constellations such as failure of measured or information values to arrive, pathological measured or information values or failure of a reaction to generate alarms. An alarm 26 is thereby forwarded to the terminal devices 20 through 22 of the shared practice 23 due to the deviation of the measured or information values from the comparison values. An alarm 27 to the patient is output given a lack of measured or information values. In the practice, the physician can call the measured or information values 28 stored in the data memory 15 with the personal computer 24.

The evaluation device 12 evaluates whether measured or information values or value constellations are to be classified as pathological As a criterion, comparison limits are thereby taken from the literature, these being stored in the data memory 15. Further, the attending physician can define individual limits for the patient. The comparison values are variable and can be adapted to the course of the therapy.

Further, an expert system can be utilized for this purpose, this interpreting the values disease-specifically and problem-specifically on the basis of rule systems or based on probabilities. An individualization of the expert system to the patient can occur, i.e. the expert system becomes more and more familiar with the patient in his monitoring during the monitoring process; as learning system, it thereby constantly makes prognoses about future measured or information values to be anticipated, these being compared to the true values. An individualized monitoring is thus realized.

In the case of complex alarms, an expert system can be utilized that assumes the process chain of reminding the patient, notifying the family physician, calling the emergency physician, organizing the transport service and/or preparing the clinic taking the availability of the alarm recipients into consideration.

The process chain is there by the totality of participating persons and institutions. These include the patient, the treatment chain comprising physician, care and transport service as well as the emergency chain with fire department routing center, emergency and transport services as well as the hospital.

Alarms, dependent on the urgency of a reaction, can be generated in different urgency stages, for example extremely urgent, urgent, routine or standard. Which measured values lead to which urgency levels can be defined with the same mechanisms as the evaluation of the measured values and can be stored in the data memory 15.

The alarm terminal devices serve the purpose of outputting the messages sent from the message service at the recipient. This purpose can be served by a specific embodiment of the terminal device for patient and/or care-giver such as PDA with modem, telephone with voice or voice-frequency signaling (DTMF), measuring instrument with integrated modem, TV set top box, cell phone, WWW form or paper form and WWW form.

The alarm terminal device, dependent on the alarm level can, for example, also be a telephone, cell phone, e-mail terminal, WWW terminal, fax machine, terminal for utilization of a proprietary service or the mailbox as well.

The system central 6 has an interface for coupling to a QS system in order to obtain a result quality under real-life conditions. Further, the central system can comprise an interface for coupling to an accounting module.

Specific embodiments of the alarm device can be an alarm triggering given pathologically or incorrectly acquired measured or information values, an alarm triggering given compliance problems on the part of the patient, an alarm triggering given a reaction time on the part of the physician to urgent messages that is too long and alarm forwarding in case the physician does not react.

Messages can be communicated, for example, via voice output by telephone, SMS, e-mail, WWW, WAP, Fax, proprietary service or letter mail.

The evaluation device 12 for the measured values and the patient data server 13 can be implemented such for data creation that the medical data are stored dependably and pseudonym-protected.

Reception devices such as, for example, a fax machine 20, personal computer 21 or a telephone 22 or cell phone are connected to the system central 6, these belonging to an on-call physician and, for example, being arranged in a shared practice 23 of physicians.

The alarm terminal device in the shared practice 23 can have a return channel 29 for transmitting therapy instructions to the patient and/or care-giver, so that a therapy can be implemented despite a spatial separation of physician and patient (tele-therapy).

Although modifications and changes may be suggested by those skilled in the art, it is in the intention of the inventors to embody within the patent warranted hereon all changes and modifications as reasonably and properly come within the scope of their contribution to the art.

We claim as our invention:

1. A method for monitoring therapy being administered to a patient, comprising the steps of:
   (a) acquiring an information value by obtaining a measurement from a patient representing a course of a therapy being administered to the patient;
   (b) designating a designated value selected from the group consisting of said information value and a calculated value calculated from said information value;
   (c) allocating a comparison value to said designated value and comparing said designated value to said comparison value in a comparison;
   (d) generating an alarm if said comparison indicates an impermissible deviation of said designated value from said comparison value;
   (e) at intervals during said course of said therapy selected from the group consisting of predetermined time intervals and variable time intervals, automatically determining, dependent on said designated value, whether a need exists to adapt said comparison value and, if so, automatically taking action selected from the group consisting of automatically changing said comparison value, and informing an agent of said need to adapt said comparison value; and (f) if said comparison value is to be adapted by an agent, automatically generating an indication to said agent of said need to adapt said comparison value.

2. A method as claimed in claim 1 wherein step (e) comprises adapting said comparison value by an authorized person as said agent.

3. A method as claimed in claim 1 wherein step (c) of adapting said comparison value comprises adapting said comparison value by an authorized entity as said agent.

4. A method as claimed in claim 1 wherein, in step (c), allocating a comparison value to said designated value comprises allocating an upper comparison value and a lower comparison value to said designated value, and wherein comparing said designated value to said comparison value comprises comparing said designated value to each of said upper comparison value and said lower comparison value.

5. A method as claimed in claim 4 wherein step (d) comprises generating an alarm if said designated value is above said upper comparison value or below said lower comparison value.

6. A method as claimed in claim 1 wherein said designated value is a current designated value, and further comprising determining said impermissible deviation for said comparison by analyzing a trend of said course of said therapy from a plurality of designated values preceding said current designated value.

7. A method as claimed in claim 1 wherein step (a) comprises acquiring a plurality of information values respectively from a plurality of measurements from said patient, and wherein the step of designating a designated value comprises designating a plurality of designated values respectively selected from the group consisting of said plurality of information values and a plurality of calculated values respectively calculated from said plurality of information values, and wherein step (c) comprises allocating a comparison value to each of said designated values and comparing the designated value to the comparison value allocated thereto in a plurality of respective comparisons.

8. A method as claimed in claim 1 wherein said information value is a current information value and wherein said designated value is a current designated value, and wherein step (e) comprises adapting said comparison value dependent on analysis of a trend of said course of said therapy determined from a plurality of designated values preceding said current designated value.

9. A method as claimed in claim 1 comprising allocating a tolerance value range to said comparison value.

10. A method as claimed in claim 1 wherein step (f) comprises automatically generating said indication to said agent if a predetermined therapy outcome, represented by said designated value, does not occur within a predetermined time duration.

11. A method as claimed in claim 10 wherein step (f) comprises allocating a time duration value to said comparison value, and defining a permissible deviation from said comparison value for said comparison, and automatically generating said indication to said agent if said designated value exhibits no permissible deviation from said comparison value within said time duration value.

12. A method as claimed in claim 1 comprising providing said agent with additional information relating to said therapy, selected from the group consisting of therapeutic information and diagnostic information, together with said indication.

13. A method as claimed in claim 12 comprising generating said additional information in a knowledge data bank and reading said additional information from said knowledge data bank for providing said additional information to said agent.

14. A method as claimed in claim 1 comprising conducting at least steps (c) and (e) in an expert system.

15. A method as claimed in claim 1 wherein step (a) comprises acquiring said information value with a measurement made by an acquisition device, and automatically communicating said information value from said acquisition device to an evaluation device, and conducting steps (b), (c), (d), (e) and (f) in said evaluation device.

16. A method as claimed in claim 1 made by said patient, entering said information value into a transmission device, establishing communication between said transmission device and an evaluation device and transmitting said information value from said transmission device to said evaluation device, and comprising conducting steps (b), (c), (d), (e) and (f) in said evaluation device.

17. A method as claimed in claim 16 wherein step (d) comprises establishing communication between said evaluation device and a reception device located remotely from evaluation device, and transmitting said alarm from said evaluation device to said reception device.

18. A method as claimed in claim 16 wherein step (f) comprises establishing communication between said evaluation device and a reception device located remotely from evaluation device, and transmitting said indication from said evaluation device to said reception device.

19. A system for monitoring therapy being administered to a patient, comprising:

an acquisition device that acquires an information value by obtaining a measurement from a patient representing a course of a therapy being administered to the patient;

an evaluation device in communication with said acquisition device for that receives said information value from said acquisition device and designate a designated value selected from the group consisting of said information value and a calculated value calculated from said information value;

said evaluation device allocating a comparison value to said designated value and comparing said designated value to said comparison value in a comparison and generating an alarm if said comparison indicates a impermissible deviation of said designated value from said comparison value;

said evaluation device, at intervals during said course of said therapy selected from the group consisting of predetermined time intervals and variable time intervals, automatically determining, dependent on said designated value, whether a need exists to adapt said comparison value and, if so, automatically taking action selected from the group consisting of automatically changing said comparison value, and informing an agent of said need to adapt said comparison value; and a reception device located at said agent, said evaluation device, if said comparison value is to be adapted by an agent, automatically generating an indication to said reception device of said need to adapt said comparison value.

20. A system as claimed in claim 19 wherein said evaluation device includes an expert system at least for adapting said comparison value to said therapy.

* * * * *